United States Patent
Bialobrzeski

(10) Patent No.: US 9,968,418 B1
(45) Date of Patent: May 15, 2018

(54) DENTAL FORCEPS WITH A POST FOR EXTRACTING TEETH

(71) Applicant: Marilyn Bialobrzeski, Mesa, AZ (US)

(72) Inventor: Marilyn Bialobrzeski, Mesa, AZ (US)

(*) Notice: Subject to any disclaimer, the term of this patent is extended or adjusted under 35 U.S.C. 154(b) by 0 days. days.

(21) Appl. No.: 15/530,269

(22) Filed: Dec. 16, 2016

Related U.S. Application Data

(60) Provisional application No. 62/388,547, filed on Feb. 1, 2016.

(51) Int. Cl.
*A61C 3/14* (2006.01)
*A61C 3/16* (2006.01)

(52) U.S. Cl.
CPC ............... *A61C 3/14* (2013.01); *A61C 3/162* (2013.01)

(58) Field of Classification Search
CPC .. A61C 3/14; A61C 3/162; A61C 3/16; A61B 17/122; A61B 17/08; A61B 17/1285; A61B 2017/00473
See application file for complete search history.

(56) References Cited

U.S. PATENT DOCUMENTS

| | | | | |
|---|---|---|---|---|
| 6,741 A * | 9/1849 | Bourne | ................... | A61C 3/16 433/154 |
| 15,215 A * | 7/1856 | Batchelder | ............... | A61C 3/16 433/154 |
| 554,844 A * | 2/1896 | Stienbarger | ............. | A61C 3/16 433/154 |
| 1,094,269 A * | 4/1914 | Taylor | ..................... | A61C 3/16 433/154 |
| 1,147,580 A * | 7/1915 | Turner | ..................... | A61C 3/16 433/154 |
| 1,386,289 A * | 8/1921 | Taylor | ..................... | A61C 3/14 433/145 |
| 1,498,285 A * | 6/1924 | Lorenz | ..................... | A61C 3/14 433/154 |
| 1,550,443 A * | 8/1925 | Maloney | .................. | A61C 3/14 433/154 |
| 2,430,271 A * | 11/1947 | Brantley | ................. | A61C 3/14 254/126 |
| 4,197,647 A * | 4/1980 | Goldenthal | .............. | A61C 3/16 433/159 |
| 4,230,454 A * | 10/1980 | Lococo | .................... | A61C 3/14 433/153 |
| 4,443,196 A * | 4/1984 | Rico | ........................ | A61C 3/14 433/158 |
| 4,798,366 A * | 1/1989 | Pearson | .................. | B25C 11/02 254/22 |
| 4,844,417 A * | 7/1989 | Schneider-Muro | .. | A61B 17/076 254/28 |
| 6,910,890 B2 * | 6/2005 | Golden | .................... | A61C 3/14 433/159 |
| 2012/0143269 A1 * | 6/2012 | Ichelmann | ......... | A61B 17/7082 606/86 R |

* cited by examiner

*Primary Examiner* — Matthew F Desanto

(57) ABSTRACT

A dental forceps that include an elongated handle and a pair of tooth engaging members or jaws extending out of the one end of the handle and a post located in the handle with a disc at the top with a ball at the other end of the post. The post ball end inserts into the post ball holder to provide a stable support so that the dentist has leverage to extract the tooth straight out. The post disc and post ball provide the forceps with side-to-side and back-and-forth movement, thus allowing the forceps to align to the growth angle of the tooth to be extracted.

3 Claims, 4 Drawing Sheets

DENTAL FORCEPS WITH A POST FOR EXTRACTING TEETH

CROSS-REFERENCE TO RELATED APPLICATION

This application claims the benefit of Provisional patent application Ser. No. 62/388,547, filed 2016 Feb. 1 by the present inventor.

FEDERALLY SPONSORED RESEARCH

None

SEQUENCE LISTING

None

BACKGROUND

Field of Invention

This invention is to change the way teeth are extracted by using a forceps with a post for greater leverage for the extraction.

Prior Art

A number of prior art devices exist for the purpose of extracting a tooth or removing a dental prosthesis, crowns and the like. The use of such devices to extract teeth is often associated with pain and unpleasantness. This invention and procedure is to extract teeth with less pain to the patient. Part of the pain originates from the simple tools that dentists currently use to extract teeth. Specifically, the forceps and elevators that are currently used by dentists require brute force to be applied by the dentist in removing the tooth. Dentists currently extract tooth twisting and turning it to break the ligaments and nerve. This results in unnecessary pain and discomfort, as the tooth must be worked out, and often the use of such tools results in damage to the socket of the extracted tooth. This invention of a post on the forceps will allow the dentists to extract the tooth straight out; no twisting or turning thus lessen the pain. The forceps with a post has a ball end that pivots in a half ball cavity that acts as a guide for the post. Thus the tooth can be extracted straight out with no twisting and turning the tooth. The distance where the forceps grip the tooth and where the post with the ball end fits into the post ball holder is the pivot point. The pivot point is used for leverage to extract the tooth straight out with less pain. The dentist's arm does not have the leverage that the post on the forceps has to extract the tooth straight out. The leverage in the forceps with the post, and using only the wrist, is a better leverage point than the dentist using his arm and forceps. There is less twisting of the dentists wrist using this forceps, thereby reducing the risk of radio-carpal conditions.

Tooth extracting tools are well known and have been in use for many years. Attempts have been made to overcome the drawback of using forceps and elevators. For example, the Dental Fulcrum Forceps disclosed in U.S. Pat. No. 1,147,580, utilizes a forceps with a post having a post ball at one end that goes into a crossbar that is placed on adjacent teeth. The post is located at the point where the two handles of the forceps are connected together. This makes the leverage point close to the tooth so it does not give as much leverage as my design. Also, the post goes into the crossbar resulting in a greater possibility for the forceps to hit the front teeth when extracting a molar. The post of patent '580 has no post disc on the top to allow for movement of the forceps to align to the tooth. Additional movement is allowed in my design due to the counter sink opening on the top of the post ball holder. The crossbar of the patent '580 has to go into the patient's mouth and rest on adjacent teeth. The crossbar is not stable and could move during the extraction. The leverage of the patent '580 would be affected by the use of the rubber on the bottom of the crossbar because the rubber would flex, not giving a positive extraction. It is unclear how the crossbar in the patient's mouth would work for the extraction of upper teeth. If the patient has any missing teeth the stability of the crossbar would be affected. For these reasons this patent '580 has not been successful.

Another tooth extractor system is disclosed in U.S. Pat. No. 4,230,454 issued to Lococo, utilizes a tooth engaging grip means selectively connectable to a lever which in turn, is rested against a base normally located on a tooth or teeth adjacent the tooth root to be extracted. This prior art tooth extractor system had the advantage of requiring less physical power from the dentists, thus enabling a more accurate operation with reduced damage of the socket of the extracted tooth. However, the tooth extractor system described in the '454 patent suffered from a relatively complex assembly of parts what would have limited its usefulness. The attachment of the tooth engaging grip means to a tooth to be extracted and the placement of the separate base component on the adjacent tooth would have required substantial skill on the part of the dentists. For at least these reasons and perhaps others, the tooth extractor system described in the '454 patent apparently did not become widely established on the market.

Another patent U.S. Pat. No. 6,910,890 issued to Richard Golden, currently marketed as the Physics Forceps, uses two gripping jaws: one has a curved hook while the second has a pad with an offsetting handle position to provide the dentists some leverage when removing teeth. When the forceps is engaged on the tooth it is held there with moderate tension for 1-2 minutes so that the fibers that connect the periodontal ligament to the alveolar bone begin to snap and at a certain point the tooth literally "Pops" loose for the socket. This method, however, does not remove the tooth straight out and still might need to twist the tooth. This forceps is for loosening the tooth not the removal. So while this patent '890 is using leverage to break the ligaments it is not using leverage for the extraction.

Various other dental forceps or so-called "fulcrum forceps" also exist in the prior art, which have found only limited success in the market. For example, U.S. Pat. No. 2,430,271 issued to Brantley, and U.S. Pat. No. 4,443,196 issued to Rico all disclose tooth extractor devices that use a fulcrum in conjunction with either a tooth clamp or a tooth root screw to facilitate removing a tooth or a tooth root from a patient. However, none of these devices provide an acceptable tool for simplifying the tooth extraction procedure and minimizing pain and unpleasantness as a tooth is worked out.

It is presently believed that there is a need for an improved device for facilitating the extraction of a tooth and a potential commercial market for a tooth extraction tool in accordance with the present invention. There should be a demand and commercial market for such devices because such devices significantly reduce the muscular strength required to extract a tooth and therefore reduce the stress and fatigue of a dentist as well as the stress on a patient. It is the general aim of the present invention to provide improved leverage for the extraction of the tooth to lessen the stress and fatigue of the dentist and to be able to pull the tooth straight out, thus lessening the pain to patient.

SUMMARY OF THE INVENTION

In accordance with the invention a tooth extracting instrument includes an elongated handle which has a pair of tooth engaging members or jaws for engaging the tooth to be extracted. The tooth extracting member or jaw engages the tooth on opposite sides. One of the elongated handles has a post holder mechanism that has a post with a disc that is attached to the post holder mechanism. The post has a ball at the other end that goes into a post holder that allows the post to go forward or backward and side to side so that the tooth extracting member can align with the tooth. The post ball holder is attached to a swing arm that is attached to the dental chair with a locking mechanism to provide a stable support.

REFERENCE NUMERALS

10. Forceps
12. Forceps Jaws
14. Post
16. Post Ball
18. Stop Pin
20. Spring
22. Ball Bearing
24. Post Disc
26. Post Disc Holder
28. Post Ball Holder
30. Set Screw
32. Tooth
34. Flat Head Screw
36. Long Set Screw
38. Counter Sink Opening
40. Post Ball Holder Center Rod

DETAILED DESCRIPTION OF THE PREFERRED EMBODIMENTS

Figure 1:
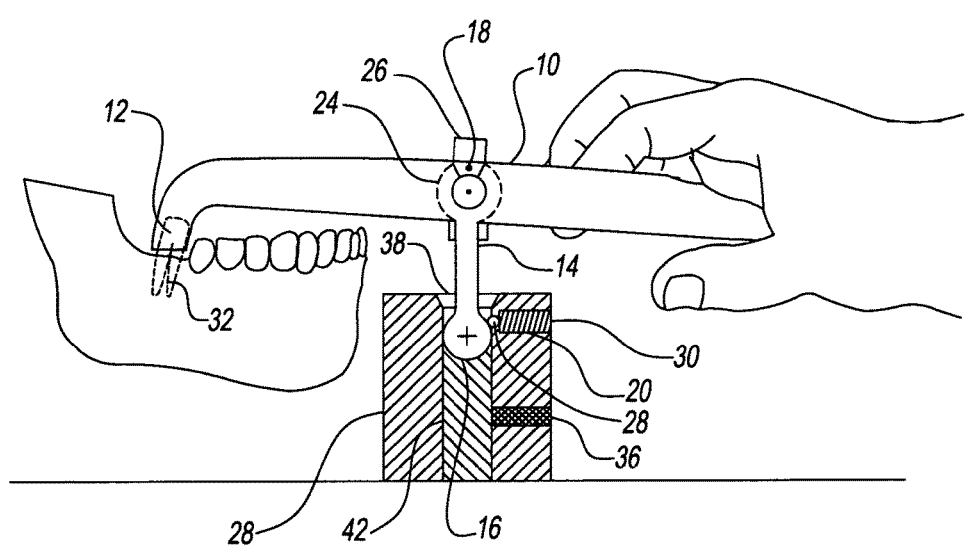
FIG. 1 is a perspective of the forceps in the post ball holder, in accordance with the invention, clasping a back molar

FIG. 1 shows a perspective view of the forceps 10, with a right side handle and left side handle having a post 14 with a post disc 24 on the upper part of the post 14. The post disc 24 is held in place by the post disc holder 26 that is lined up in the center of the forceps jaws 12. The post disc 24 has a slot in the top to form a stop when the stop pin 18 is screwed through the forceps 10 handle and into the post disc holder 26. The lower part of the post 14 has a post ball 16 that fits into the post ball holder 28. The post 14 is held in place in the post ball holder 28 by a ball bearing 22 held in place with a spring 20 and set screw 30 in three places around the post ball holder 28. There is a post ball holder center rod 40 that can be adjusted by a long set screw 36. When the forceps 10 is placed into the post ball holder 28 and is aligned with the tooth 32, that can be done by the counter sink opening 38 allowing the post to move, the dentist now has the leverage to extract the tooth 32 straight out.

Figure 2:
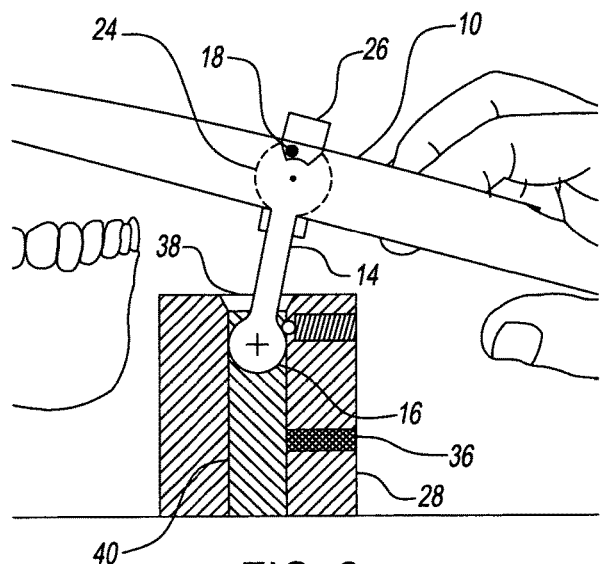
FIG. 2 is a perspective showing the forceps in the post ball holder with the post having a disc on the top with a stop and moved back in the post ball holder as shown in FIG. 1
Figure 3:
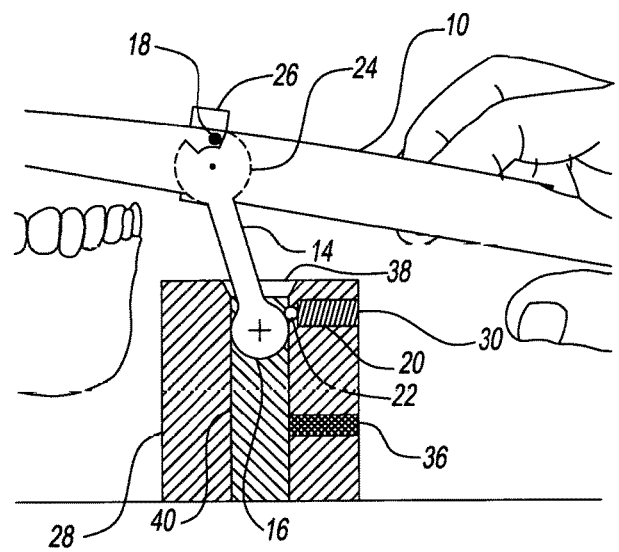
FIG. 3 is a perspective showing the forceps in the post ball holder with the post having a disc on the top with a stop and moved forward in the post ball holder as shown in FIG. 1 and FIG. 2

FIG. 2 and FIG. 3 show a closer view of FIG. 1 with the post 14 moved backward and forward in the post ball holder 28 because of the counter sink opening 38 at the top of the post ball holder 28 and the post disc 24 having the stop pin 18.

Figure 4:
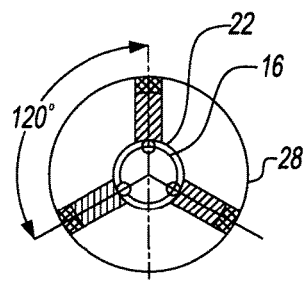
FIG. 4 is a top view of the post ball holder as shown in FIG. 1, FIG. 2 and FIG. 3

FIG. 4 shows a top view of the post ball holder 28 as shown in FIG. 1, FIG. 2, and FIG. 3. It also shows the placement of the ball bearings 22 at 120 degrees on the round post ball holder 28. The post ball 16 is shown in the center of the post ball holder 28.

Figure 5:
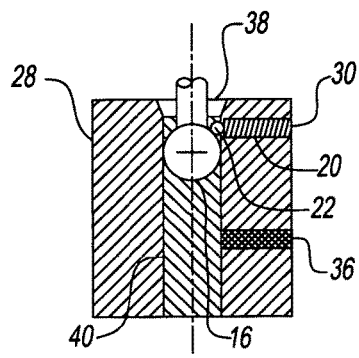
FIG. 5 is a lateral cross-section view of the post ball holder as shown in FIG. 1, FIG. 2 and FIG. 3

FIG. 5 shows a cross section view of the post ball holder 28 as shown in FIG. 1, FIG. 2, and FIG. 3. It shows the post ball 16 in held in place in the post ball holder 28 by a ball bearing 22 held in place with a spring 20 and set screw 30 in three places around the post ball holder 28. There is a post ball holder center rod 40 that can be adjusted by a long set screw 36 during manufacturing.

Figure 6:
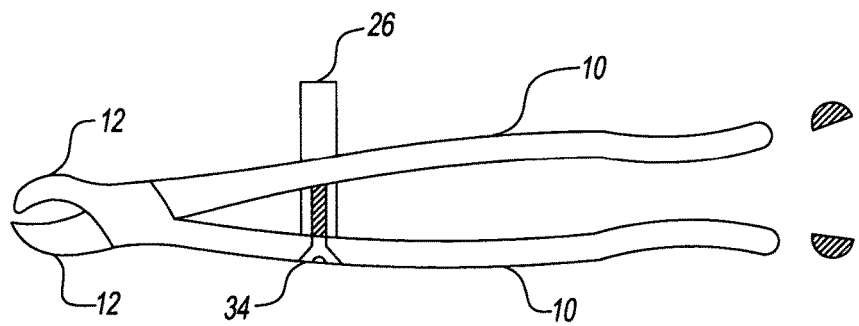
FIG. 6 is a top view of the forceps with the post disc holder as shown in FIG. 1, FIG. 2 and FIG. 3

FIG. 6 shows a top view of the forceps 10 with the forceps jaws 12, as shown in FIG. 1,FIG. 2, and FIG. 3, with the post disc holder 26 held in place with a flat head screw 34.

Figure 7:
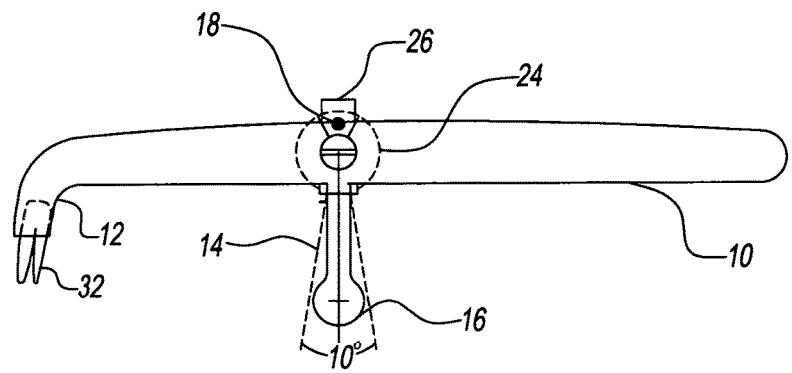
FIG. 7 is a side view of the forceps with the disc holder and post as shown in FIG. 1, FIG. 2, FIG. 3, and FIG. 6

FIG. 7 is a side view of the forceps 10 with forceps jaws 12 holding a tooth 32, as shown in FIG. 1, FIG. 2, FIG. 3, and FIG. 6 with the post disc 24 in the post disc holder 26, and the stop pin 18. The range of movement of the post 14 is shown to be 10 degrees.

Figure 8:
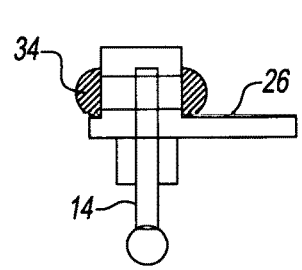
FIG. 8 is a front view of the post disc holder as shown in FIG. 1, FIG. 2, FIG. 3, FIG. 6, and FIG. 7

FIG. 8 is a front view of the post disc holder 26 as shown in FIG. 1, FIG. 2, FIG. 3, FIG. 6, and FIG. 7. This shows the post 14 placed in the post disc holder 26 and held in place with a flat head screw 34.

Figure 9:
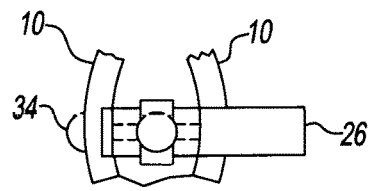
FIG. 9 is a top view of the post disc holder as shown in FIG. 1, FIG. 2, FIG. 3 FIG. 6 and FIG. 7 and FIG. 8

FIG. 9 shows a bottom view of the post disc holder 26 as seen in FIG. 1, FIG. 2, FIG. 3, FIG. 6, and FIG. 7. This shows the forceps 10 with the post disc holder 26 centered in the forceps and held in place with a flat head screw 34.

Figure 10:
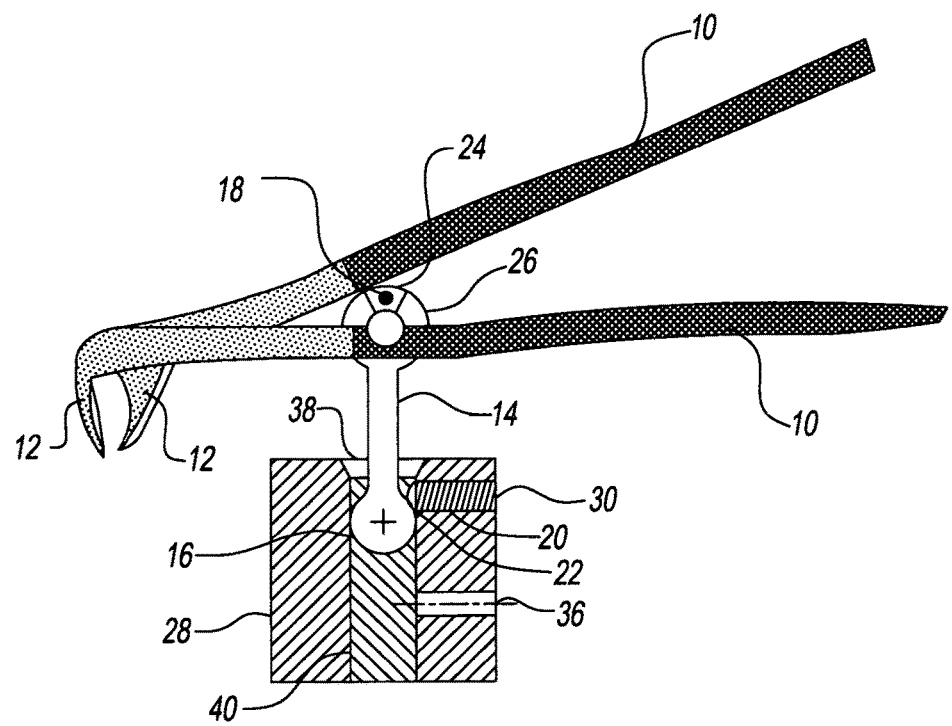
FIG. 10 is a side view of a beaks forceps with a post and post disc holder

FIG. 10 is a perspective view of the forceps 10, where the handles are upper and lower instead of side by side, having a post 14 with a post disc 24 on the upper part of the post 14. The post disc 24 is held in place by the post disc holder 26 that is lined up in the center of the forceps jaws 12 on the lower handle. The post disc 24 has a slot in the top to form a stop when the stop pin 18 is screwed through the forceps 10 handle and into the post disc holder 26. The lower part of the post 14 has a post ball 16 that fits into the post ball holder 28. The post 14 in held in place in the post ball holder 28 by a ball bearing 22 held in place with a spring 20 and set screw 30 in three places around the post ball holder 28. There is a post ball holder center rod 40 that can be adjusted by a long set screw 36. When the forceps 10 is placed into the post ball holder 14 and is aligned with the teeth, that can be done by the counter sink opening 38 allowing the post to move, the dentist now has the leverage to extract the tooth straight out.

Figure 11:
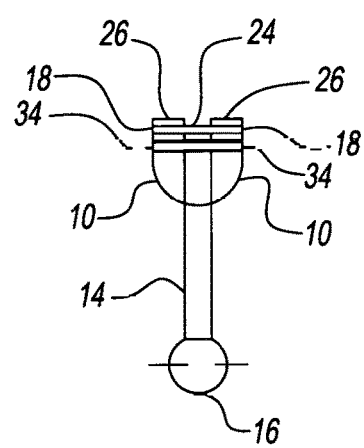
FIG. 11 is a cross section of the post disc holder as shown in FIG. 10

FIG. 11 shows a front view of the post disc holder 26 and post 14 with the post ball 16 and the post disc 24 as shown in FIG. 10. This shows the post 14 placed in the post disc holder 26 so that is aligns in the center of the forceps handle 10 and held in place with a flat head screw 34 and the stop pin 18 in the post disc holder.

CONCLUSION

Tooth extracting tools are well known and have been in use for many years. When a conventional dental forceps is used to extract a tooth the dentist must apply considerable holding force to the forceps while simultaneously applying extracting force to the instrument. Any slipping or loosening of the grip on the tooth may cause the crown of the tooth to be broken off at or near the gum line, requiring surgical removal of the remaining portion of the tooth below the gum line. Excessive gum damage may also result as well as more pain to the patient.

By having a post on the forceps with a ball end that pivots on the rod in the post ball holder and the counter sink opening of the holder provides leverage to extract the tooth straight out, not to twist and turn. The distance where the forceps grip the tooth and where the post with the ball end fits the half ball is the pivot point which is used for leverage to extract the tooth straight out with less pain. The post ball holder can be attached to the swing arm that is attached to the dental chair using a locking mechanism to provide a stable support.

It is important to remember that when the ligaments, nerves and blood vessels are severed and when the tooth is extracted straight out the chances are lessened of breaking the root of the tooth. The dentist arm does not have the leverage that the forceps with a post has to extract the tooth straight out. It would be easier for the dentist to extract a molar because of the leverage. The post in the forceps provides a stable support and a leverage point that is better than the dentist just using his arm and forceps. With the post there is more accuracy in the extraction of the tooth. The post ball holder provides a positive position for the extraction. As seen the FIG. 1 the handles are side by side while FIG. 10 shows a forceps with the handles are upper and lower. The post disc holder is shaped differently for the forceps handle in FIG. 1 and FIG. 10 but function is the same. In both cases the post disc holder is located in the center of the forceps jaw.

What is claimed is:

1. A dental forceps for extracting teeth comprising:
    a pair of forceps arms, each arm comprising a handle end and a jaw end, the arms pivotally connected at a point intermediate either end;
    a post having a lower part with a post ball and an upper part with a post disc, the post disc having a slot in a top portion with stops;
    a post disc holder;
    a post ball holder;
    a stop pin is screwed through the forceps arms and into the post disc holder;
    wherein the post disc at the upper part of the post is attached to the forceps arms by the post disc holder and the post ball at a lower end of the post is attached into the post ball holder and the stop pin is configured to go through the slot in the top of the post disc holder and engage the stops to allow movement of approximately 4 to 6 degrees in backward and forward directions;
    whereby, the dental forceps is configured to form a pivot point for leverage when the handle end of the forceps are pushed down to extract the tooth straight out.

2. The dental forceps of claim 1, wherein the post ball holder is configured to allow the dental forceps to go back and forth and side to side approximately 5 degrees from a center point of the post ball holder.

3. The dental forceps of claim 1, wherein the post and the jaw ends are aligned when the post is located in the post ball holder so that the dental forceps is configured to provide leverage for allowing extraction of a tooth straight out.

* * * * *